(12) United States Patent
Sakaguchi et al.

(10) Patent No.: US 9,835,611 B2
(45) Date of Patent: Dec. 5, 2017

(54) STRESS HISTORY MEASUREMENT METHOD AND STRESS SENSOR

(71) Applicant: Japan Agency for Marine-Earth Science and Technology, Kanagawa (JP)

(72) Inventors: Arito Sakaguchi, Kanagawa (JP); Hide Sakaguchi, Kanagawa (JP)

(73) Assignee: JAPAN AGENCY FOR MARINE-EARTH SCIENCE AND TECHNOLOGY, Kanagawa (JP)

( * ) Notice: Subject to any disclaimer, the term of this patent is extended or adjusted under 35 U.S.C. 154(b) by 0 days.

(21) Appl. No.: 14/893,804

(22) PCT Filed: May 26, 2014

(86) PCT No.: PCT/JP2014/063845
§ 371 (c)(1),
(2) Date: Nov. 24, 2015

(87) PCT Pub. No.: WO2014/192697
PCT Pub. Date: Dec. 4, 2014

(65) Prior Publication Data
US 2016/0103114 A1    Apr. 14, 2016

(30) Foreign Application Priority Data
May 27, 2013 (JP) ................... 2013-110668

(51) Int. Cl.
*G01N 33/00* (2006.01)
*G01N 33/38* (2006.01)
(Continued)

(52) U.S. Cl.
CPC .......... *G01N 33/385* (2013.01); *G01L 5/0047* (2013.01); *G01M 5/0033* (2013.01); *G01N 33/383* (2013.01); *G01N 2203/0212* (2013.01)

(58) Field of Classification Search
CPC .............. G01N 33/385; G01N 33/383; G01N 2203/0212; G01M 5/0033; G01L 5/0047
(Continued)

(56) References Cited

U.S. PATENT DOCUMENTS 4,444,924 A * 4/1984 Grimmer ................ C04B 26/14
                                                    523/445
5,690,729 A * 11/1997 Jones, Jr. ................ C04B 28/02
                                                    106/682
(Continued)

FOREIGN PATENT DOCUMENTS

DE   WO 2013041570 A1 *  3/2013 ............. C04B 26/06
DE   WO 2014127809 A1 *  8/2014 ............. C04B 26/02
(Continued)

OTHER PUBLICATIONS

Ferrill et al. "Calcite twin morphology: a low-temperature deformation geothermometer". Journal of Structural Geology vol. 26, Issue 8, Aug. 2004, pp. 1521-1529. Accessed [Online] Jan. 8, 2017. <http://ac.els-cdn.com/S0191814104000021/1-s2.0-S0191814104000021-main.pdf?>.*
(Continued)

*Primary Examiner* — Jonathan Dunlap
(74) *Attorney, Agent, or Firm* — Lucas & Mercanti, LLP

(57) ABSTRACT

It is an object to provide a stress history measurement method and a stress sensor by which the stress history of an object being measured can be measured easily with high accuracy over a wide stress measurement range. In the stress history measurement method, the stress history to which the object being measured has been subjected is measured on the basis of the ratio of twinned calcite particles after the object to be measured has been subjected to an external force, the object having a stress sensor embedded therein and capable of being deformed elastically when being subjected to the external force, the sensor including a
(Continued)

number of calcite particles. The stress sensor is configured such that a number of calcite particles are hardened by a resin with adjacent particles kept in contact with each other.

4 Claims, 1 Drawing Sheet

(51) Int. Cl.
  *G01M 5/00* (2006.01)
  *G01L 5/00* (2006.01)
(58) Field of Classification Search
  USPC .................. 73/803, 787, 770, 768, 762
  See application file for complete search history.

(56) References Cited

U.S. PATENT DOCUMENTS

| | | | | |
|---|---|---|---|---|
| 6,221,935 | B1* | 4/2001 | Hashimoto | C04B 26/18 523/218 |
| 8,066,812 | B2* | 11/2011 | Wu | C04B 28/32 106/685 |
| 8,661,913 | B2* | 3/2014 | Sakaguchi | C04B 40/0096 73/803 |
| 2009/0272052 | A1* | 11/2009 | Eide | C04B 28/02 52/251 |
| 2009/0286076 | A1* | 11/2009 | Xu | C09D 5/22 428/339 |
| 2009/0301355 | A1* | 12/2009 | Eide | C04B 14/048 106/737 |
| 2011/0232394 | A1* | 9/2011 | Sakaguchi | C04B 40/0096 73/803 |

FOREIGN PATENT DOCUMENTS

| | | |
|---|---|---|
| EP | 2 357 459 A1 | 8/2011 |
| JP | H11295198 A | 10/1999 |
| JP | 2004101322 A | 4/2004 |
| JP | 2008144280 A | 6/2008 |
| JP | 2008-286689 A | 11/2008 |
| JP | 4295334 B2 | 4/2009 |
| JP | 2012033902 A | 2/2012 |
| WO | 2010055584 A1 | 5/2010 |

OTHER PUBLICATIONS

Chen et al. "Deformation twinning and residual stress in calcite studied with synchrotron polychromiatic X-ray microdiffraction". Physics and Chemistry of Minerals. vol. 38, Issue 6; Jun. 2011. pp. 491-500. <https://link.springer.com/article/10.1007/s00269-011-0422-7>.*
Notification of Reason for Refusal dated Sep. 6, 2016 from corresponding Japanese Application; Japanese Patent Application No. 2013-110668; English translation of Notification of Reason for Refusal; Total of 7 pages.
S. Shibuya, et al; Calcite sosho henkei no rikigaku model ni . . . ; Proceedings of the Annual conference of the Japan Society of Civil Engineers; vol. 65; 2010; CS08-001; pp. 1-2.
Sakaguchi, et al; Elastic stress indication in elastically rebounded rock; Geophysical Research Letters; vol. 38; Issue 9; 2011; L09316; pp. 1-4.
International Search Report dated Jun. 17, 2014 for PCT/JP2014/063845.
Extended European Search Report dated Dec. 9, 2016 from the corresponding European Application No./Patent No. 14805133.7-1559 / 3006912 PCT/JP2014063845; Applicant: Japan Agency for Marine-Earth Science and Technology; Total of 9 pages.
Non Patent Literature by Fu S-Y Et Al, "Characterization of tensile behaviour of hybrid short glass fibre/calcite particle/ABS composites"; Composites, IPC Business Press Ltd. Haywards Heath, GB, vol. 29, No. 5-6, 1998, pp. 575-583, XP004120868.

* cited by examiner

[FIG. 1]
(a)
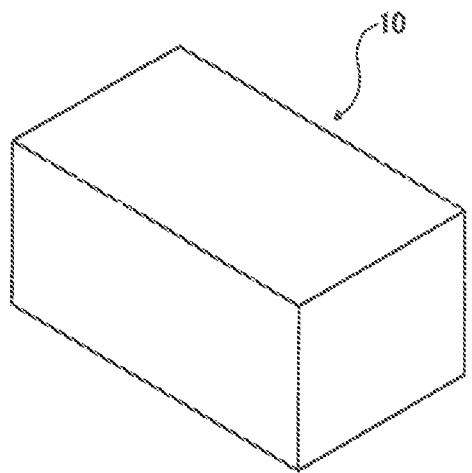
(b)
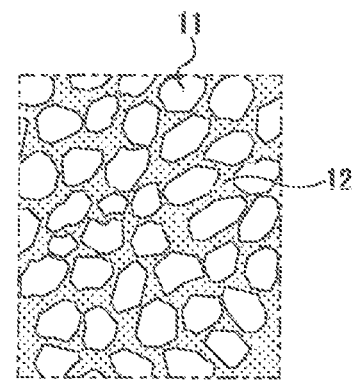
[FIG. 2]
(a)
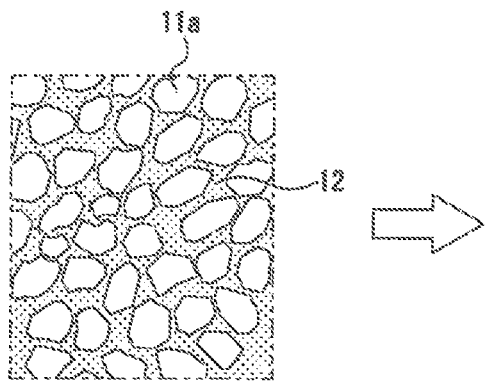
(b)
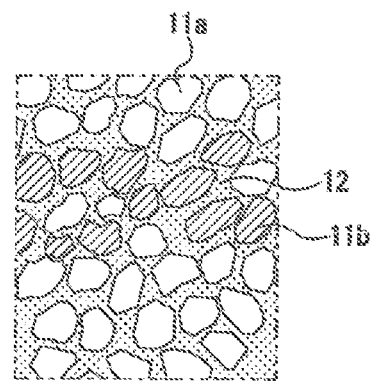

STRESS HISTORY MEASUREMENT METHOD AND STRESS SENSOR

CROSS REFERENCE TO RELATED APPLICATION

This Application is a 371 of PCT/JP2014/063845 filed on May 26, 2014 which, in turn, claimed the priority of Japanese Patent Application No. 2013-110668 filed May 27, 2013, both applications are incorporated herein by reference.

TECHNICAL FIELD

The present invention relates to a stress history measurement method and a stress sensor.

BACKGROUND ART

There are certain methods currently available for measuring internal stress in a concrete structure, for example, a method of measuring current stress by providing in advance a marker or a sensor (for example, see Patent Literature 1) or a method of sampling a core and making an estimation from the amount of rebound or the AE Kayser effect (for example, see Patent Literature 2).

Then, for example, suppose that a concrete structure is subjected momentarily to an intensive force due to a natural disaster such as an earthquake or a tornado or an accident such as a collision with a high-speed traffic vehicle. Even in this case, the fact is that when the concrete structure itself may not be destroyed but only elastically deformed, and then restored from the elastic deformation by the external force being subsequently released, the magnitude and the distribution of the force to which the concrete structure has been subjected cannot be accurately estimated.

In such a case, it is conceivable to analyse the stress history of the concrete structure, for example, by making an estimation by simulation or by sampling a core at an expectedly significant point so as to estimate the maximum amount of stress by the acoustic emission (AE measurement) of the core. However, any one of the methods cannot serve to provide an evaluation with high reliability. That is, the estimation method by simulation has a problem that the result of a simulation remains still ambiguous because the magnitude and the direction of a suddenly acting external force are only a matter of speculation in the first place.

Furthermore, the AE measurement cannot be made with high accuracy because the AE measurement is conducted by loading a core material onto a mechanical tester and then estimating a preceding maximum stress on the basis of the point of increase of a microfracture sound. Furthermore, the AE measurement has still another problem, for example, that the AE measurement cannot serve as a reproducible test because the direction of the maximum, stress at the time of occurrence of an event cannot be identified, and only a limited number of inspections can be conducted on the entire structure because the AE measurement is a destructive testing.

Still furthermore, also conceivable is such a method of placing a number of strain gauges in an entire concrete structure and then analysing the stress history of the concrete structure by monitoring the same all the time. However, such a method is not practical for a typical building, and embedding a sensor, which is a foreign matter, in the concrete may also lead to non-uniformity, thereby causing the concrete to be destroyed.

As means to address the problems mentioned above, the present inventors have proposed a method of mixing, particle by particle, synthetic calcites serving as a stress indicator into an object to be measured; and repeatedly measuring a number of calcite particles one by one with a microscope for the twinning density of the calcite particles, thereby estimating the stress that has acted upon the entire object to be measured on the basis of the average value of the resulting twinning density (see Patent Literature 3).

Such a measurement method is realistic because the method employs the property of calcite crystals, so that the need for maintenance is eliminated and measurements may be conducted only when required.

CITATION LIST

Patent Literature

Patent Literature 1: Japanese Patent Application Laid-Open No. 2004-101322
Patent Literature 2: Japanese Patent Application Laid-Open. No. Hei. 11-295198
Patent Literature 3: Japanese Patent No. 4295334

SUMMARY OF INVENTION

Technical Problem

However, such a method requires a skilled, measurement technique as well as measurements of a number of calcite particles, thus requiring time and manpower.

Furthermore, to measure the twinning density of calcite particles, it is required that at least two pairs of twin crystals be formed of the calcite particles. Furthermore, to detect a low stress, there was a restriction, on the crystalline size that a calcite particle having a crystalline size of 1 mm or greater, for example, had to be employed. The reason for this is that the less the acting external force, the greater the twin crystal separation becomes.

Furthermore, the fact is that there still remains a technical problem with preparing calcite particles having a crystalline size of 1 mm or greater in large quantity.

The present invention was developed in view of the circumstances mentioned above. It is therefore an object of the present invention to provide a stress history measurement method and a stress sensor by which the stress history of an object to be measured can be measured easily with high accuracy in a wide stress measurement range.

Solution to Problem

The stress history measurement method of the present invention comprises measuring a stress history which has been subjected to an object to be measured on the basis of a ratio of twinned calcite particles after the object being measured has been subjected to an external force, the object having a stress sensor embedded therein and capable of being deformed elastically when the object is subjected to an external force, the sensor including a number of calcite particles.

In the stress history measurement method of the present invention, it is preferable that calcite particles that originally have no twin crystals are employed.

Furthermore, in the stress history measurement method of the present invention, it is preferable that, as the stress sensor, one that has a number of calcite particles hardened with a resin is employed.

Still furthermore, in the stress history measurement method of the present invention, the maximum stress that has acted on the entire object to be measured is estimated on the basis of a ratio of twinned calcite particles to a plurality of calcite particles having an exposed crystalline plane in a region to be inspected, the region being at least a part of the object to be measured.

The stress sensor of the present invention comprises a number of calcite particles being bound or hardened with a resin in a state that adjacent particles are kept in contact with or close proximity to each other.

Advantageous Effects of Invention

According to the stress history measurement method of the present invention, it is enough to measure only the ratio of twinned calcite particles that remain even after an external force acted on an object to be measured has been released. It is thus possible for anyone to measure easily with high accuracy the stress history, for example, the maximum stress of the object being measured.

Furthermore, it is enough to check for the presence or absence of twinning only, thereby eliminating a restriction on the crystalline size of the calcite particles, that would be otherwise required for a method of measuring the twinning density of calcite particles. For example, it is thus possible to take advantage of synthetic calcite particles having a crystalline size that permits mass production.

Furthermore, use of calcite particles originally having no twinning makes a sufficiently wide measurable range available, so that, for example, even when a low stress has acted on the object to be measured, the stress history can be measured. In addition, when a portion on which no stress has acted is to be measured, no twin crystal needs to be counted, which implements a high efficiency.

Still furthermore, employed as the stress sensor is what is called an aggregate of calcite particles in which a number of calcite particles are hardened by a resin with adjacent particles kept in contact with each other, so that the number of available calcite particles that are required on a surface to be inspected for measurement is ensured, and it is possible to provide measurement results with high reliability as well as facilitate the measurement itself.

BRIEF DESCRIPTION OF DRAWINGS

FIG. 1 shows explanatory views illustrating an example of a stress sensor of the present invention; (a) a schematic perspective view illustrating an entire structure, and (b) a schematic diagram illustrating a particle structure.

FIG. 2 shows conceptual diagrams illustrating calcite particles on which external force acts to thereby cause twinning.

DESCRIPTION OF EMBODIMENTS

Now, a description will be made in detail to an embodiment of the present invention.

An object to be measured according to the stress history measurement method of the present indention is a product or a structure member made of, for example, concrete or a composite material that is predominantly made of cement, and the object to be measured includes a stress sensor of a number of calcite particles embedded therein.

FIG. 1 shows explanatory views illustrating an example of the stress sensor of the present invention. (a) is a schematic perspective view illustrating an entire structure, and (b) is a schematic diagram, illustrating a particle structure.

The stress sensor 10 is formed of a number of calcite particles (monocrystal) 11 being hardened by a binder resin 12, for example, in the shape of a rectangular parallelepiped with a grain support structure found among the calcite particles 11. That is, in the stress sensor 10, adjacent calcite particles are kept in contact with or close proximity to each other, allowing the structure to be held in between the particles.

The binder resin 12 that constitutes the stress sensor 10 is not limited to a particular one insofar as the resin has the properties below:

(A) Flowability before being cured;
(B) A small volume shrinkage rate when being cured; and
(C) A high hardness after being eared, for example, a higher strength than that of an object to be measured.

Such resins may include, for example, an epoxy resin, more specifically, an ultra-low viscosity epoxy resin "E205" (Trade name; available from Nichika Inc.).

As the calcite particles 11, any calcite particle is acceptable, naturally occurring (including those having subjected to a certain stress event) or artificially synthesized, insofar as the calcite particle has been checked for the presence or absence of twinning (the initial state has been checked). However, the calcite particle preferably has no twinning in an original state. When for example, synthetic calcite particles having no twinning are employed as the calcite particles 11, it is possible to provide a sufficiently wide measurable range because of a measurement principle reason for detecting the ratio of twinned calcite particles. Thus, it is possible to measure, for example, low stress of about a few Mpa. On the other hand, when a portion on which no stress has acted is measured, no twin crystals have to be counted, thus implementing a high efficiency.

It is preferable for the calcite particles 11 to have a particle diameter (crystalline size), for example, within the range of 60 μm to 2000 μm (both inclusive), more specifically about 200 μm. For example, this particle diameter is equivalent to the particle diameter of sand particles that are fine concrete aggregates. Here, "the particle diameter of the calcite particle" is defined as the shorter diameter of a rectangle that circumscribes the maximum projected shape.

For example, if the particle diameter of the calcite particles 11 is excessively large, the particle diameter may be greater than that of sand particles that are fine concrete aggregates. This raises a problem that the calcite particles would act not as a stress meter but as a support of the framework itself. On the other hand, if the particle diameter of the calcite particles 11 is excessively small, there is a problem that measurements may be conducted with difficulty.

The percentage of content of the calcite particles 11 is preferably 60 to 80 vol %, for example. This allows 300 for example, or more calcite particles having, a particle diameter of 200 μm for example, to exist on a measurement cross section in a region to be inspected, so that an intended stress measurement (inspection) can be positively made with nigh reliability.

The aforementioned stress sensor 10 can be manufactured as follows.

That is, a predetermined amount of calcite particles 11 is charged into a mold at room temperature under a normal atmospheric pressure, and then a binder resin 12 is charged into the mold in a vacuum or under a reduced pressure. Then, the binder resin 12 is cured under atmospheric pressure, thereby providing the aforementioned stress sensor 10.

The stress sensor 10 is configured such that a number of calcite particles 11 are hardened with the binder resin 12 with adjacent particles kept in contact with or close proximity to each other, in other words, constructed as a so-called aggregate of calcite particles. Thus, according to the stress sensor 10, the number of calcite particles that are required for intended measurement can be made available on a surface to be inspected. Thus, it is possible to provide measurement results with high reliability as well as facilitate the measurement itself.

In the stress history measurement using the aforementioned stress sensor 10, for example, when an external force including shearing force acts on a concrete product or a concrete structure to such an extent that does not cause any destruction thereto but only an elastic deformation, a twin crystal is formed as shown in FIG. 2 on a particular crystalline plane of the calcite particles depending on the magnitude of the external force. Even after the external force is removed and the object to be measured is restored from the elastic deformation, the twinned calcite particles will not disappear. Thus, the calcite particle serves as what is called "a micro stress meter." Here, FIG. 2(a) illustrates the initial state, and (b) illustrates a state after the external force is removed. The twinning of the calcite particles does not occur on ail the calcite particles, so that there is a mixture of non-twinned calcite particles 11a and twinned calcite particles 11b.

Then, as a result of intensive studies conducted by the inventors, it was found that for example, within a stress range equivalent to a low stress of about a few Mpa to at least a rupture strength of ordinary concrete (for example, about 36 MPa), the ratio or twinned calcite particles 11 increased in proportion to the magnitude of an acting external force, in other words, the ratio of the twinned calcite particles 11 had the linear relation with the magnitude of the external force acted.

It was also found that applying a stress equal to or greater than the history stress to those that have already been subjected to a certain stress event leads to an increase in the number of twinned calcite particles.

Thus, by measuring the ratio of twinned calcite particles, it is possible to measure the stress history, for example, the maximum stress to which the concrete product or the concrete structure has been subjected.

How, a description will be made to a specific example of the stress history measurement method. First, when the aforementioned stress sensor 10 is embedded in the object to be measured, the stress sensor 10 is taken out of the object to be measured, and then part of a surface of the stress sensor 10 is selected as a region to be inspected. On the other hand, when the aforementioned stress sensor 10 is embedded in the surface of the object to be measured, part of the surface of the stress sensor 10 is selected, as a region to be inspected, without taking the stress sensor 10 out of the object to be measured.

Then, the surface of the region to be inspected is polished to thereby expose the crystalline plane of a plurality of calcite particles as an inspection surface. Here, the size of the region so be inspected is not limited to a particular value but may be appropriately set according to the purpose of the inspection.

Then the entire inspection surface is scanned with an optical microscope, for example, to conduct an image analysis of the calcite particles having an exposed crystalline plane, thereby checking for the presence or absence of twinned calcite particles. Then, the process computes the ratio of twinned calcite particles to a plurality of calcite particles present in the region being inspected of a predetermined size. The presence or absence of twinned calcite particles can be readily determined because for example, the refractive index or the reflectivity changes as the crystalline grid of the calcite particle is deformed. Furthermore, it is also possible to compute the ratio of twinned calcite particles by detecting a change in light transmittance of the entire stress sensor 10 between before the application of an external force (the initial state) and after the application and subsequent release of the external force.

As described above, since the ratio of twinned calcite particles present within the region to be inspected of a predetermined size tends to increase as the external force increases, it is possible to estimate the absolute value and the distribution of stresses to which the entire object to be measured has been subjected on the basis of the ratio of the twinned calcite particles.

Then, according to such a stress history measurement method, it is enough to measure only the ratio of twinned calcite particles that remain even after the external force acted on the object to foe measured has been removed. It is thus possible for anyone to measure easily with high accuracy the stress history of the object being measured, for example, the maximum stress.

Furthermore, it is enough to check only for the presence or absence of twinned calcite particles. This eliminates a restriction on the crystalline size of the calcite particles that would be otherwise required for a method of measuring the twinning density of the calcite particles 11. For example, it is thus possible to take advantage of synthetic calcite particles having a crystalline size that permits mass production.

Furthermore, use of the calcite particles 11 originally having no twinning makes a sufficiently wide measurable range available, so that, for example, even when a low stress has acted on the object to be measured, the stress history can be measured. In addition, when a portion on which no stress has acted is to be measured, the twin crystal needs not to be counted, which implements a high efficiency.

Now, an example experiment will be shown below to demonstrate the effects of the present invention.

Example Experiment 1

About 0.5 g of monocrystal synthetic calcite particles having no twinning were charged into a mold having a rectangular parallelepiped cavity of 5 mm×5 mm×10 mm. Here, the calcite particles had a particle diameter (crystalline size) of 200 μm, and the percentage of content of calcite particles was about 70 vol %.

Then, the mold was accommodated in a vacuum, chamber so as to fill an epoxy resin "E205" (Trade name; made by Nichika Inc.) into gaps between the calcite particles in a vacuum. The vacuum level was set to be 1 kPa or less. Subsequently, while bubbles remaining between the calcite particles were crushed under atmospheric pressure to thereby eliminate the gaps, the epoxy resin was cured by being left for 24 hours under atmospheric pressure at room temperature, thereby producing a test specimen of the stress sensor according to the present invention.

In this test specimen, by employing a field of view region 10 mm in diameter of an optical microscope, 300 calcite particles or more were found in the field of view region, and grain support structures were observed with the calcite particles.

Furthermore, by a uniaxial compression test that conforms to JIS 1108 (a method for testing the compression, strength, of concrete) except for the specification of the sample sire, the compression, strength of the test specimen was measured, so that the test specimen was found to have a compression strength of about 37 MPa.

The test specimen obtained as described above was found to have a ratio of twinned calcite particles of substantially 0% under no load condition. The test specimen was checked for the presence or absence of twinned calcite particles by employing some region of the test specimen as a region to be inspected, polishing a surface to thereby expose the crystalline plane of a plurality of calcite particles, and observing the crystalline plane of the calcite particles with the optical microscope.

Then, the same uniaxial compression test as mentioned above was conducted on the test specimen with various appropriate loads applied thereto so as to examine the ratio of twinned calcite particles with respect to the magnitude of the loads. As a result, the ratio of the twinned calcite particles was found to be 18% when a load of 41% the compressionstrength of the test specimen (15 MPa) acted thereon. Furthermore, the ratio of twinned calcite particles was found to be 27% when a load of 55% the compression strength of the test specimen (20 MPa) acted thereon, while the ratio of twinned calcite particles was found to be 44% when a load of 100% the compression strength of the test specimen (37 MPa) acted thereon.

From the results above, it was found that the ratio of twinned crystal particles increased in proportion to the magnitude of acting loads.

While the invention has been described above with reference to the embodiment, it is to be understood that the invention is not limited to the aforementioned embodiment, but various changes and modifications may be made thereto.

For example, in the stress history measurement method of the present invention, it is also acceptable to employ, as a stress sensor, a calcite particle itself which is mixed with component materials of an object to be measured. For example, when a composite material predominantly made of cement, for example, concrete is employed as the object to be measured, calcite particles may also be mixed previously therewith and dispersed therein in place of an aggregate, for example, part of sand.

Furthermore, in an embodiment of the present invention, the stress sensor is not limited in shape to a rectangular parallelepiped but may be changed as appropriate depending on the purpose. For example, the stress sensor may also take a spherical shape, in the case of which the stress sensor can be constructed with no anisotropy with respect to the direction of stress.

INDUSTRIAL APPLICABILITY

The present invention may be preferably applied to concrete structures, for example, those structures such as dams or power plants which are subjected to stress all the time, small bridges or harbor breakwaters, or a small-scale structure such as a condominium.

In particular, the present invention is useful when a small-scale structure is subjected to force to such an extent that the structure is not destructed and thereafter the damage to the structure is quantitatively evaluated. More specifically, for example, when a small-scale structure is subjected to shaking due to an earthquake of a seismic intensity of 5 upper or seismic intensity of 6 and then it is tested whether the structure maintains a predetermined strength, or when the local stress concentration that follows the deterioration of the structure itself is monitored, the present invention can be used, thereby showing promise for improvement of safety evaluation.

Furthermore, for example, according to the present invention, when the strength of a concrete structure, particularly, reinforced concrete structure with steel bars arranged is evaluated, the strength of the concrete itself can be measured, which thus shows promise for correctly evaluating not only whether the steel bars have been arranged in an adequate manner but also whether the concrete materials themselves are appropriate ones.

REFERENCE SIGNS LIST

10 stress sensor
11 calcite particles
11a non-twinned calcite particles
11b twinned calcite particles
12 binder resin

The invention claimed is:

1. A stress history measurement method comprising:
   embedding a stress sensor in an object, the object being elastically deformable when subject to an external force, the stress sensor comprising a plurality of calcite particles;
   inspecting the stress sensor to determine a ratio of twinned calcite particles in the stress sensor after an application of an external force to the object, the ratio being twinned calcite particles in the stress sensor after the application of the external force to the object to untwinned calcite particles in the stress sensor before the application of the external force to the object; and
   determining a stress history of the object based on the ratio of the twinned calcite particles present in the stress sensor after the application of the external force to the object.

2. The stress history measurement method according to claim 1, wherein the calcite particles in the stress sensor before the application of the external force to the object have no twinned crystals.

3. The stress history measurement method according to claim 1, wherein the stress sensor comprises the calcite particles and a hardened resin.

4. The stress history measurement method according to claim 1, wherein the inspection of the stress sensor is conducted in a region of the stress sensor having an exposed crystalline plane of the calcite particles, and the stress sensor is embedded in the object during the inspection.

* * * * *